Figure 1:
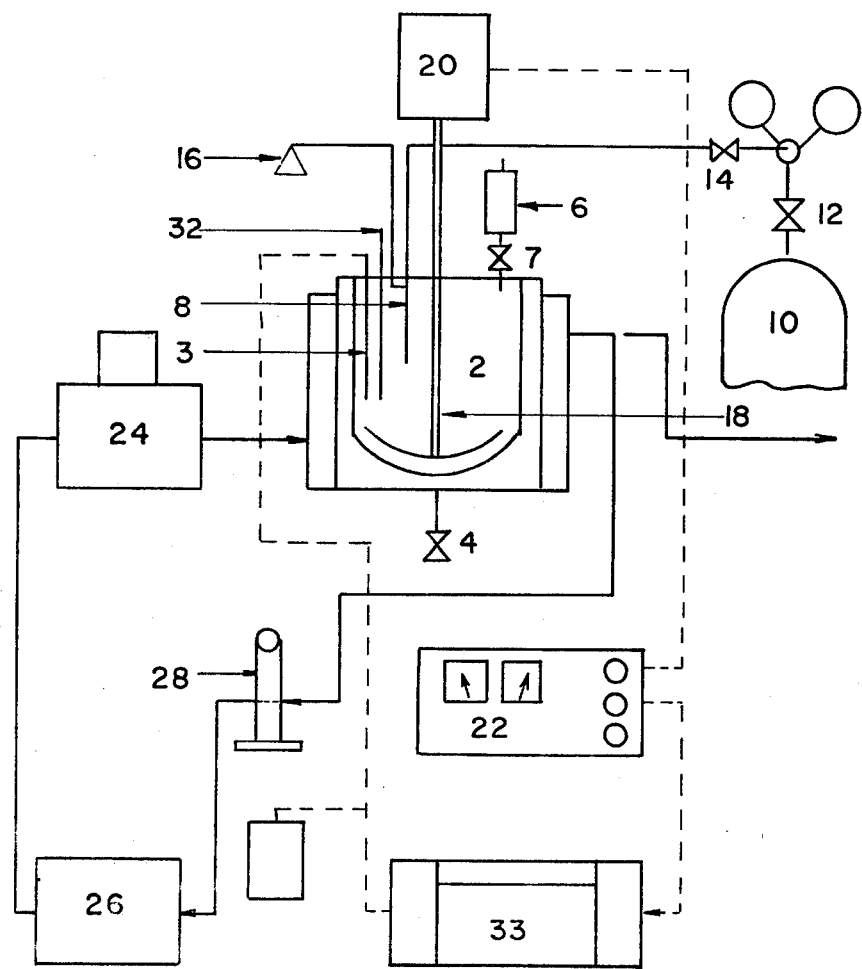

United States Patent [19]

Wisniak et al.

[11] 4,130,495
[45] Dec. 19, 1978

[54] LIQUID JOJOBA OIL DERIVATIVES

[75] Inventors: Jaime Wisniak; Hanoch Benajahu, both of Beer Sheva, Israel

[73] Assignee: Ben-Gurion University of the Negev Research and Development Authority, Beer Sheva, Israel

[21] Appl. No.: 743,012

[22] Filed: Nov. 18, 1976

[30] Foreign Application Priority Data

Dec. 2, 1975 [IL] Israel .................................. 48585

[51] Int. Cl.$^2$ .................... C08G 75/00; C10M 1/38
[52] U.S. Cl. ................................ 252/48.4; 252/48.6; 260/399
[58] Field of Search ..................... 252/48.6, 48.4; 260/399

[56] References Cited

U.S. PATENT DOCUMENTS

| 2,054,283 | 9/1936 | Ellis .................................... 260/399 |
| 2,179,062 | 11/1937 | Smith et al. ....................... 252/48.4 |
| 2,212,899 | 8/1940 | Flaxman ............................ 252/48.6 |

OTHER PUBLICATIONS

Gisser et al., "Jojoba Oil as a Sperm Oil Substitute", Mar. 1976, AD Report A024123.

Primary Examiner—Delbert E. Gantz
Assistant Examiner—Joan Thierstein
Attorney, Agent, or Firm—Lawrence Rosen; E. Janet Berry

[57] ABSTRACT

A non-factice sulfohalogenated jojoba oil characterized by a M.W. under 4,500, an I.V. greater than 5, a sulfur content below 8.7% and having a sulfur to halogen mole ratio of about 1.1:1.0 to about 1.0:1.1.

12 Claims, 7 Drawing Figures

LIQUID JOJOBA OIL DERIVATIVES

The present invention relates to a liquid jojoba oil derivative and lubricating oil additives containing the same. More particularly the present invention relates to a non-factice sulfohalogenated jojoba oil which is especially adapted to serve as a substitute for sulfurized sperm whale oil.

In an effort to protect the world's dwindling population of sperm whale and seven other whale species, in late 1970 the U.S. Government included them in the list of Endangered Species and banned imports of oil, meat and other products derived from whales. At the time of the ban sperm oil consumption in the United States was about 40–50 million pounds per year, with half that figure utilized in lubricant applications. The unique liquid wax produced by sperm whales was of importance in various lubricant applications such as automotive transmission fluids, metal working oils, industrial and automotive gear lubricants and tractor hydraulic fluids.

Sulfurized sperm oil was used in many lubricants because it has a combination of properties not matched by other available additives: Solubility in high viscosity paraffinic oils, low tendency to form sludge on oxidation, good antiwear, friction an extreme pressure (EP) properties, as well as compatibility with other additives such as lead naphthenate. It was also available in large quantities and at low cost, a fact that eliminated significant research over the years on synthetic replacements.

The ban on the use of sperm oil gave place to an intensive search for substitutes. The many approaches tried can be summarized in two: (1) Development of a totally synthetic mixture similar to that of sperm oil, and (2) development of a replacement having different chemical composition but similar selling price - performance relationship for sulfurized additives.

Sperm oil differs in chemical structure from most other fatty oils in that it is largely composed of monoesters derived from $C_{16}$ and $C_{18}$ alcohols, 60% unsaturated, and $C_{14}$, $C_{16}$, $C_{18}$ and $C_{20}$ carboxylic acids, 75% unsaturated. The mechanical properties of the oil are attributed to its monoolefinic structure.

No single natural or synthetic replacement with the unique qualities of sperm oil has yet been found but several publications have shown that the oil extracted from jojoba (Simmondsia chinensis) may prove to be an excellent substitute if it becomes available in commercial quantities. A recent publication of the Committee on Jojoba Utilization of the National Academy of Sciences (Anonymous, 1975) has concluded that among other things jojoba oil can duplicate sperm oil performance and be used as a substitute for the complete range of its uses, without requiring major reformulations.

Jojoba is an evergreen shrub of the Buxaceae family that grows in semi-desert areas and yields a nut that contains about 50% of an oil composed of monoesters of the $C_{20}$ and $C_{22}$ alcohols and acids, each with one double bond. Jojoba oil is a liquid wax that contains two double bonds in each constituent molecule. The N.M.R. spectrum of the raw material was studied in a 1:1 volume solution in benzene. The hydrogen atoms next to the double bond, and the allylic hydrogen appear with a shift of 5.5 ppm and 2.1 ppm respectively. The hydrogen atoms in position $\alpha$ to the carboxylic group appear with shifts 4 ppm and 2.15 ppm. The methylenic hydrogens and those in the —$CH_3$ groups appear with shifts of 1.1 ppm and 0.8 ppm respectively. The area of the different peaks shows that that of hydrogen atoms belonging to the double bonds is double that of hydrogen atoms in position $\alpha$ to the oxygen. Also the area of the aliphatic hydrogens is substantially larger than that of the other peaks.

Jojoba possesses several advantageous characteristics over sperm oil: (1) It has no fishy odor, (2) the crude oil contains no stearins and requires little or no treatment for most industrial purposes, (3) it can take larger amounts of sulfur, (4) it does not darken on sulfurization and (5) the highly sulfurized oil is liquid, whereas sperm oil when highly sulfurized requires addition of mineral oil in order to remain liquid.

Gisser et al. "Jojoba oil as a sperm oil substitute" Publication U.S. Army, Frankford Arsenal, Pittman-Dunn Laboratory, Philadelphia (1973) have recently conducted a thorough comparison of the mechanical properties of jojoba oil and sperm oil sulfurized by standard procedures. Both sulfurized oils were diluted to different concentrations in a 100 SUS at 37.8° C. naphthenic oil and in a 150 SUS at 99° C. midcontinent bright stock oil. The diluted oils were evaluated on the Four-Ball EP and Falex Testers, and Four-Ball Wear Testers. Results of the experimental work showed that sulfurized jojoba and sulfurized sperm oils were essentially equivalent in improving the load-carrying capacity under extreme-pressure conditions of both naphthenic and bright stock base oils. Both undiluted sulfurized oils exhibited approximately equivalent E.P. properties. Small amounts of sulfurized jojoba and sulfurized sperm oil were also equally effective antiwear additives to the naphthenic and bright stock oils. Shop drilling and tapping operations confirmed that sulfurized jojoba could replace sperm oil in practical operations.

In U.S. Pat. No. 2,450,403 (Wells) there is described the sulfurization of jojoba oil for use as lubricants and extreme pressure additives. Wells sulfurized the oil by heating it with stirring to 250° C. and adding a quarter of the weight of sulfur. When the temperature reached 300° F. a second quarter was added; at 350° F. a third: and at 365° F. the fourth quarter of sulfur was introduced. The temperature was rapidly taken to 380° F. and heating discontinued. Appropriate thermal treatment of the mixture assured that it remained liquid in spite of the high sulfur content (+30%).

More specifically said patent claims a process of making a liquid highly sulfurized jojoba bean oil containing up to about 31% combined sulfur, which comprises heating jojoba bean oil and adding sulfur portionwise thereto on the up-heat between 250° F. and 400° F. whereby the reaction product when cold is a solid when formed with large amounts of sulfur and thereafter continuing the heating at between 350° F. and 400° F. for up to about 20 minutes until the reaction product when cold is liquid.

Despite said publications it has not heretofor been suggested that sulfohalogenation of jojoba oil instead of sulfurization would produce a product of superior properties as described hereinafter.

In U.S. Pat. No. 2,054,283 (Ellis) there is described the treatment of jojoba oil with sulfur chloride to produce a jojoba oil factice which factice is claimed. A reading of said patent shows, however, that Ellis' work was intended primarily to the manufacture of a factice which was readily soluble in various aromatic and aliphatic solvents and could be incorporated in rubber, linoleum, paints and varnishes, plastics, and the like. His process was based on disolution of jojoba oil in an equal volume of benzene and addition of 9–10% volume (oil) of $S_2Cl_2$. The reactants were mixed and allowed to stand until reaction was completed. Evaporation of the solvent yielded a rubber-like, sticky, light amber colored, tasteless mass, substantially free of acidity and soluble in various hydrocarbon solvents. The reaction could also be conducted in the absence of a solvent and the HCl formed was eliminated by hot water washed. Thus while said patent claims inter alia the reaction product of jojoba oil with a sulfur chloride a careful reading of said patent and its examples shows that said patent is in fact solely directed to the combination of jojoba oil and sulfur chloride to produce a jojoba oil factice.

According to the present invention it has now been discovered that by adjusting reaction conditions and reactant ratios there could be produced a non-factice sulfohalogenated jojoba oil adapted for use as a lubricant or extreme pressure additive having superior properties over sulfurized jojoba oil.

Thus the present invention provides a non-factice sulfohalogenated jojoba oil characterized by a M.W. under 4,500, an I.V. (iodine value) greater than 5, a sulfur content below 8.7% by weight and having a sulfur to halogen mole ratio of about 1.1:1.0 to about 1.0:1.1, and preferably a mole ratio of about 1:1.

Preferably the sulfohalogenated liquid jojoba oils according to the present invention are ones wherein the sulfur content by weight is between about 6.5 and about 8.5% and most preferably between about 7 and 8%.

While the following description and examples will be directed to sulfochlorination, it is believed that sulfobromination will give similar results and consequently sulfobrominated jojoba oil is also intended to be included in the present invention.

In preparing the compositions of the present invention it has been found that the reaction between jojoba oil and $S_2Cl_2$ caused addition of chlorine and sulfur in the same ratio in which they were present in $S_2Cl_2$, that is about 1:1. The results plotted pointed out that when the double bonds were completely saturated the content of sulfur was 8.7% and that of chlorine 9.5%.

The linear relation found between the number of double bonds and the chlorine and sulfur contents indicated that the basic reaction was one of addition to the double bond, with little or no substitution. The latter phenomenon would have increased the sulfur and chlorine content without changing the iodine value. The molecular weight and viscosity of the sulfurized oil showed a parallel behavior with sulfur content and a large increase in both parameters was observed in the small range of 7 to 8.5% sulfur. These two facts indicated that a polymer was being formed, an assumption that was further supported by the proposed reaction mechanism. On the basis of these facts emerged a picture of the attack of the double bond by $S_2Cl_2$ wherein a sulfur bridge was normally formed between two different oil molecules and the resulting structure was composed of units of the following partial formula:

Figure 2:
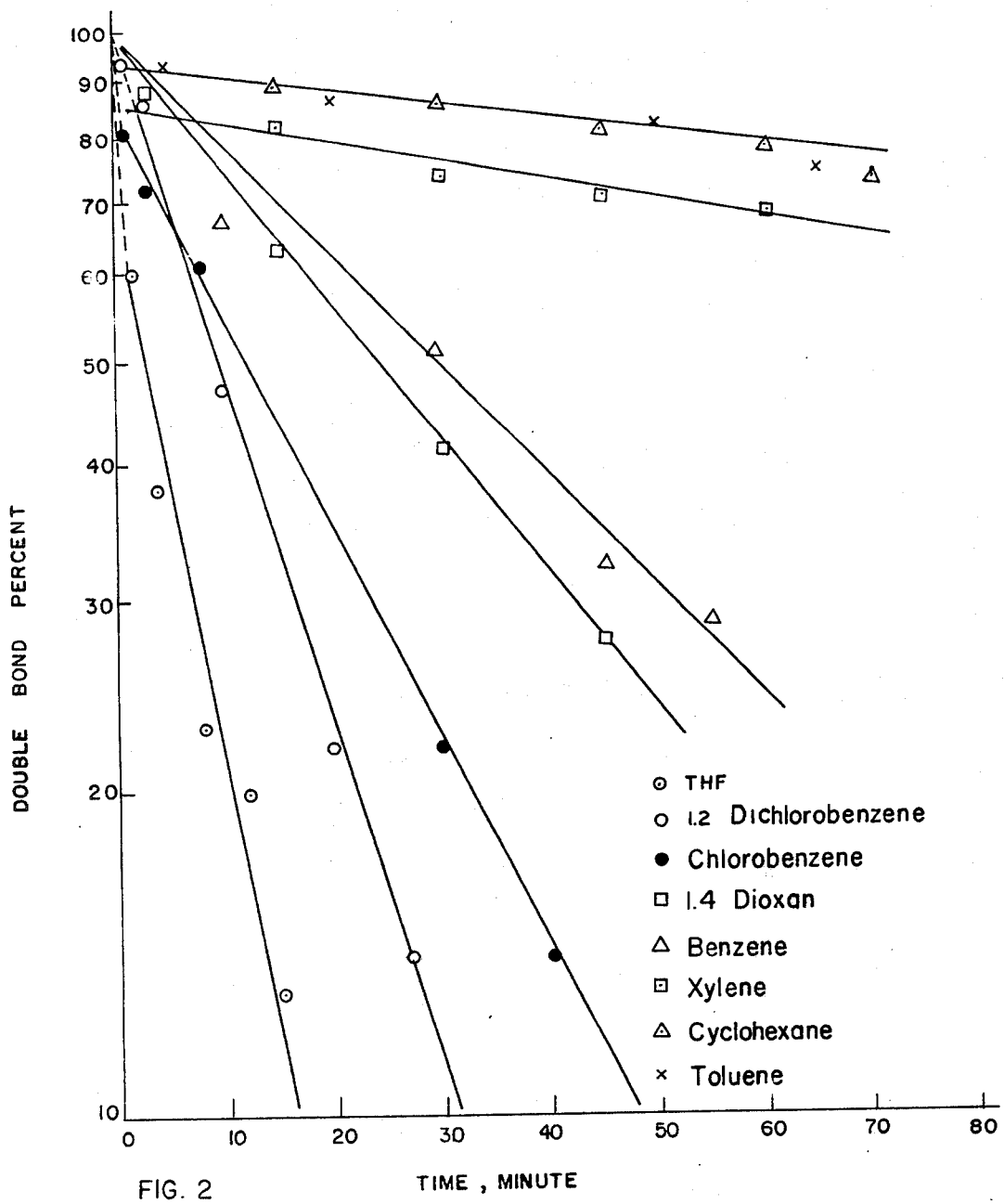
Figure 3:
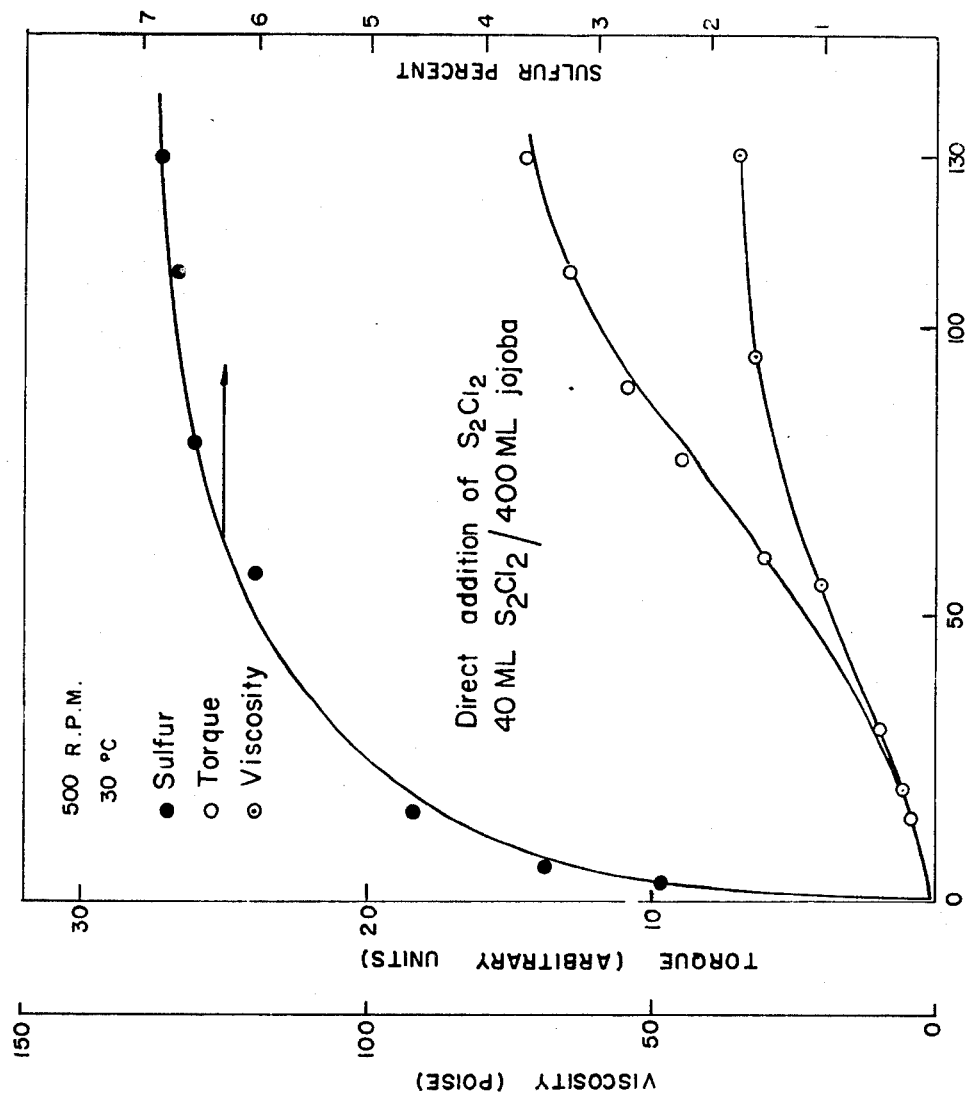
Figure 4:
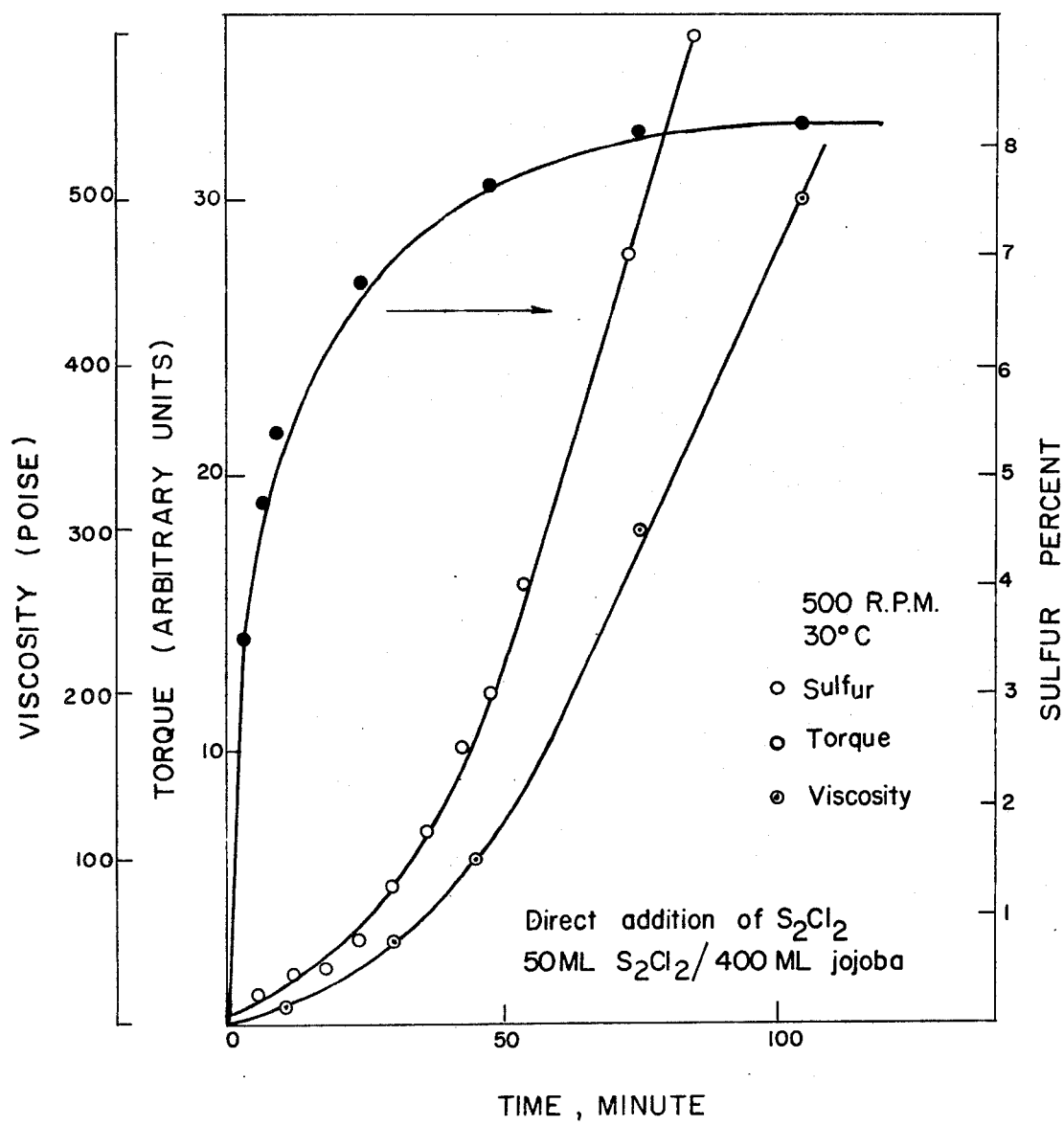
Figure 5:
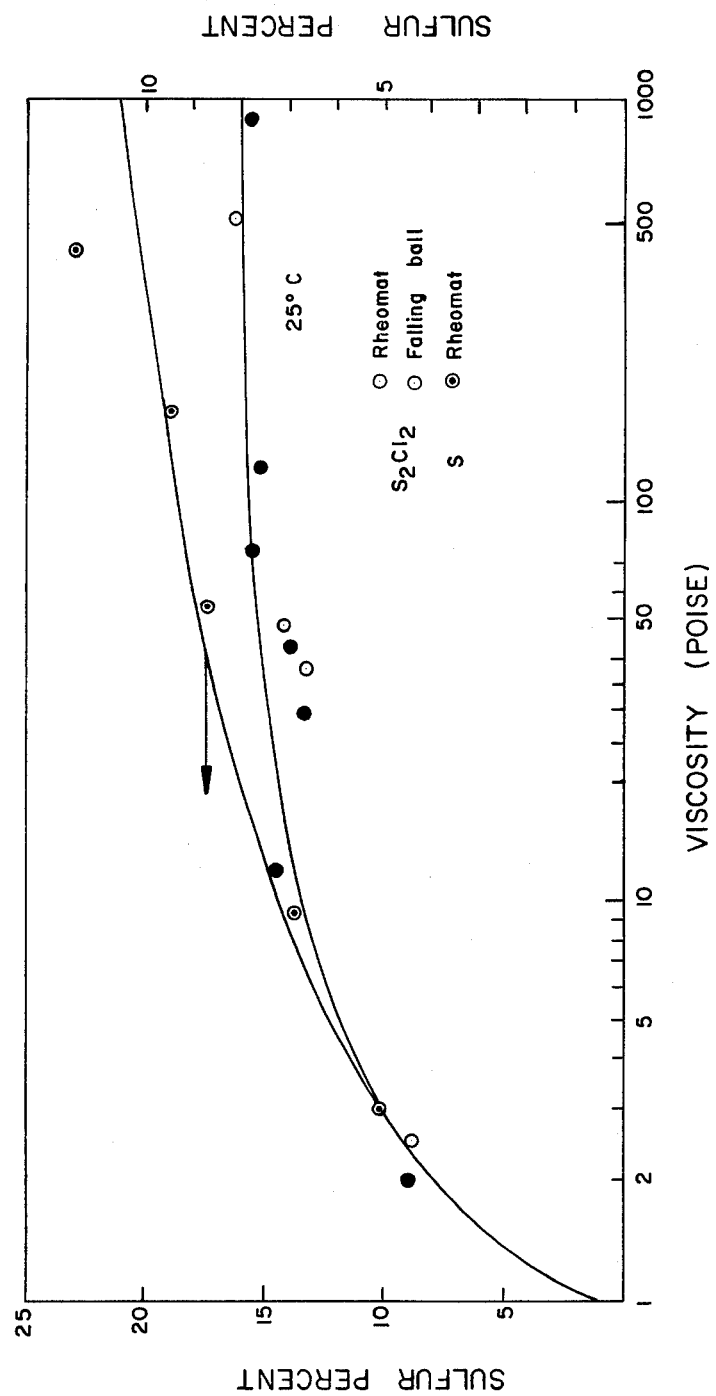
Figure 6:
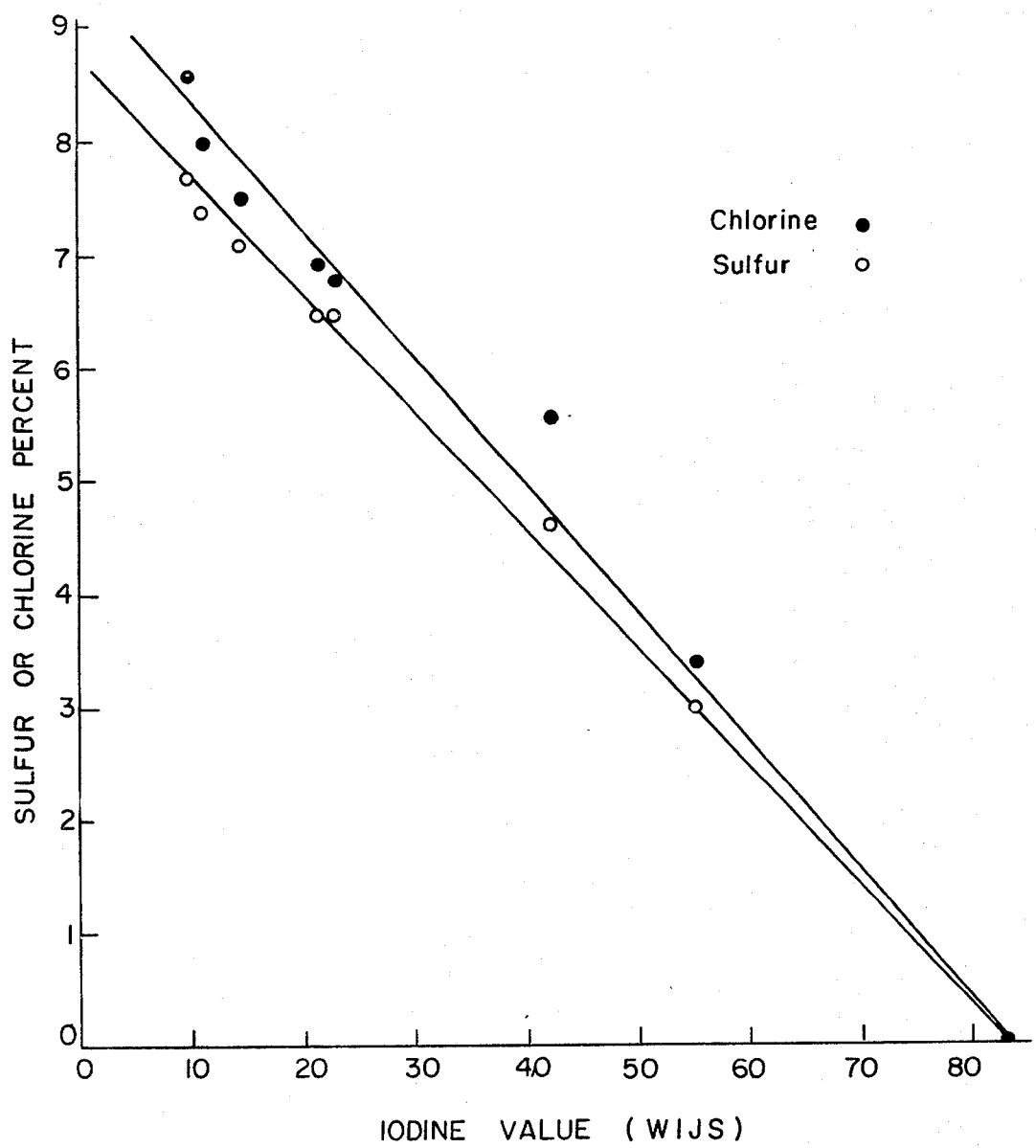
Figure 7:
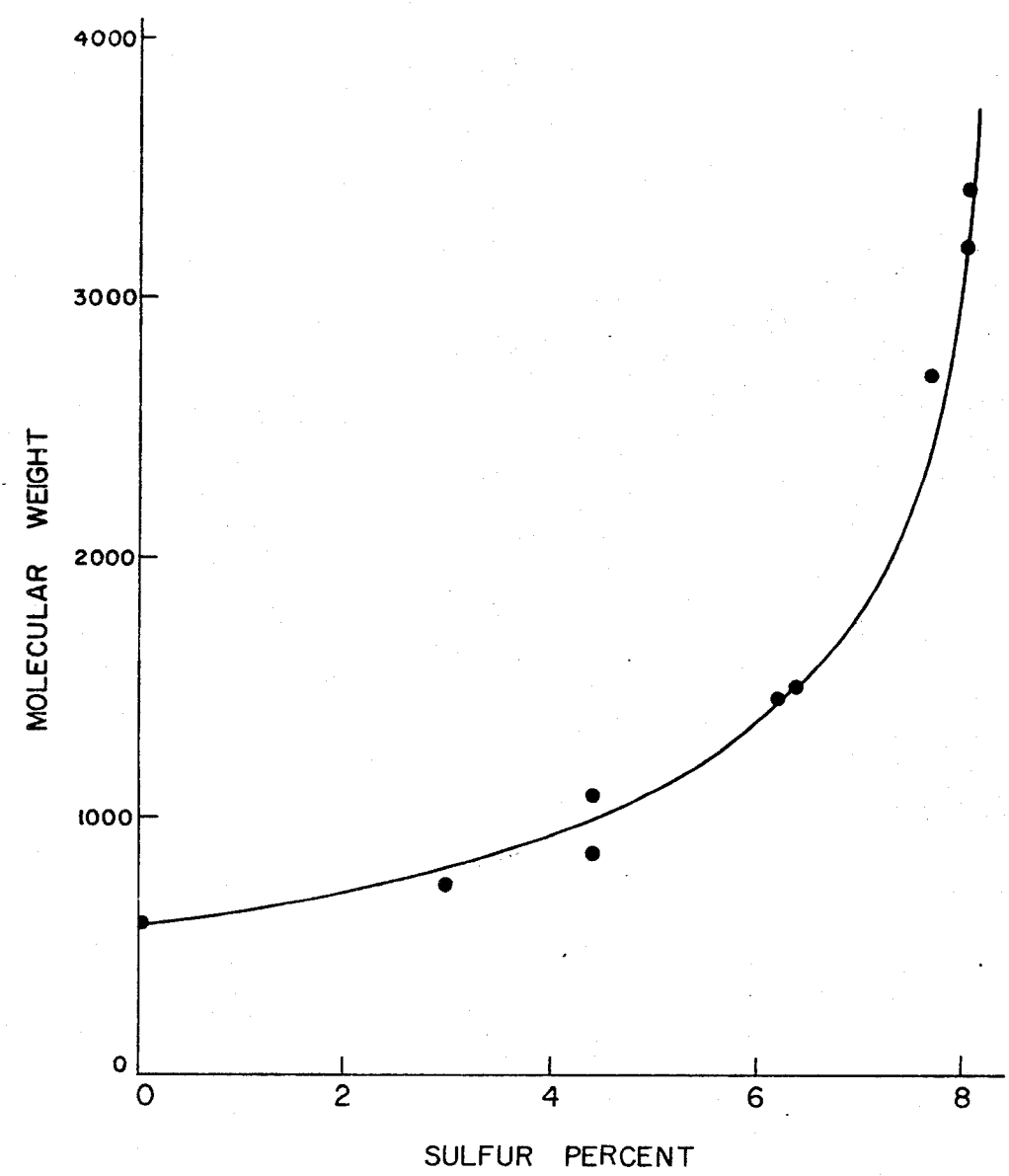

In order that the invention may be understood more fully, reference should be had to the following illustrative description read in conjunction with the accompanying figures in which:

FIG. 1 is a schematic plan of the apparatus used to prepare and test the product of the present invention, and FIGS. 2–7 are graphic tables of test results in which FIG. 2 graphically illustrates the influence of different solvents on the disappearance rate of the double bond;

FIG. 3 graphically illustrates viscosity, sulfur percent and torque change during a reaction using less than a stoichiometric amount of $S_2Cl_2$;

FIG. 4 graphically illustrates viscosity, sulfur percent and torque change during a reaction using more than a stoichiometric amount of $S_2Cl_2$;

FIG. 5 graphically illustrates viscosity as a function of sulfur percent for sulfur monochloride as compared with sulfur;

FIG. 6 graphically illustrates iodine values as a function of sulfur or chlorine percent; and FIG. 7 graphically illustrates molecular weight as a function of sulfur percent.

Inspection of the N.M.R. spectra of jojoba oil sulfurized with $S_2Cl_2$ and sulfur showed the similar nature of the sulfur peaks and the absence of the chlorine peak at 4.3 ppm. The N.M.R. spectrum of jojoba oil sulfurized with sulfur did not allow to determine clearly the degree of bridging, but a reasonable guess was that the bridge would be built by two sulfur molecules so that the amount of sulfur needed to open the double bond would be double of that needed for sulfurization with $S_2Cl_2$. The height of the chlorine peak at a shift of 4.3 ppm was equal to that of the sulfur peak, corroborating the assumption that the opening of every double bond involved the addition of one chlorine atom and one sulfur atom.

The difference between sulfurization with sulfur and sulfurization with $S_2Cl_2$ is then the formation of two bridges between two sulfur atoms in the first case, and only one bridge in the second case. This difference in structure results in the fact that the mechanical properties of jojoba oil sulfurized with $S_2Cl_2$ substantially different from those of jojoba oil sulfurized with sulfur.

Kaufman et al., Fette U. Seifen, 44, 337 and 1390 (1937a, 1937b) reacted different liquid fats with $S_2Cl_2$ vapors in a dessicator. The analysis of the sulfur content showed that within an hour it achieved an almost constant value and the following increases were very slow because of the resistance to $S_2Cl_2$ diffusion caused by the higher viscosity.

The phenomenon described above of significant mass transfer resistances did not present itself when the present reaction was carried out in the presence of solvents. The dilution effect of the solvent was instrumental in maintaining a low relative viscosity during the course of the reaction. This fact was illustrated very clearly by plotting in a semilog graph the variation of double bonds contents or sulfur contents with time, when $S_2Cl_2$ was added in one portion, with or without solvents. A straight line was always obtained when the reaction occurred in the presence of a solvent.

In order to study the mechanism of the reaction runs were performed using solvents with different polarity. The solvents studied included nitrobenzene, tetrahydrofuran (THF), chlorobenzene, 1-2 chlorobenzene, 1-4 dioxan, benzene, toluene, xylene, cyclohexane, and $CCl_4$. Most of the results are reported in FIG. 2. It is seen that there is a clear relation between the rate of disappearance of the double bonds and the polarity of the solvent: Larger dielectric constants are conducive to higher rates of reaction. With nitrobenzene, for example, the double bonds totally disappeared within 1.5 minutes. The value of the dielectric constant was not the only significant parameter. In FIG. 2 it can be seen that there was a significant difference in the rate of reaction in benzene and cyclohexane, in spite of the fact that both solvents have essentially the same dielectric constant. The reaction rates with or without $CCl_4$ were similar, except for the fact that $CCl_4$ did not dissolve the reaction product.

Examining again the results plotting in FIG. 2 shows that addition of solvents like cyclohexane, toluene and xylene caused a modest decrease in the number of double bonds present. All these solvents had a relatively low dielectric constant and the overall effect could be considered as one of dilution alone: Addition of a solvent of this class decreased the viscosity and increased the dilution and the probability that two reacting molecules would be within a certain distance, at a given time. For higher dielectric constants a new factor made an important constribution to the overall phenomena. Higher dielectric constants were seen to give place to faster rates of double bond disappearance. A polar solvent will attract intermediate compounds that are in a polar form and will enlarge their average life by enough time to enable them to react before they disappear.

It is believed however that the valve of the dielectric constant is not enough to describe the overall picture. Solvents with the same dielectric constant did not necessarily produce the same rate of reaction and some difference must have also been due to the difference in their molecular structure. With solvents of the same family like benzene, monochlorobenzene and 1-2 dichlorobenzene the rate of reaction varied almost linearly with the dielectric constant. On the other hand, solvents like THF, with an ether linkage, or benzene and xylene with $\pi$ electrons, deviates substantially from the linear behavior.

Thus while absolute conclusions have not yet been drawn it already appears from the results obtained that it is preferably for the reaction to be carried out in a solvent and that the solvent should preferably be cyclic and preferably have a high dielectric constant, e.g., between about 2 and 15. Preferred among the solvents tried are benzene chlorobenzene, 1,4-dioxan and dichlorobenzene in which the reaction takes place at a moderate rate.

While the invention will now be described in regard to general operating equipment and techniques and in connection with certain preferred embodiments, it will be understood that it is not intended to limit the invention to these particular embodiments. On the contrary, it is intended to cover all alternatives, modifications and equivalent arrangements as may be included within the scope of the invention, as defined by the appended claims. Nevertheless, it is believed that the embodiments of the invention will be more fully understood from a consideration of the following illustrative description. It is stressed however, that the particulars discussed are by way of example and for purposes of illustrative discussion only and are presented in the cause of providing what is believed to be the most useful and readily understood description of the principles and conceptual aspects of the invention. In this regard no attempt is made to show structural details of the apparatus used to prepare and test the claimed compositions in more detail than is necessary for a fundamental understanding of the invention the description making apparent to those skilled in the art how the several forms of the invention may be embodied in practice.

The general view and arrangement of the experimental setup appears in FIG. 1. The main piece of equipment was reactor 2 built from a one-liter capacity, double-wall resin flask. The vessel could be emptied through a valve 4 connected to its bottom, this same valve was used for sampling purposes. The cover of the reactor carried five necks that permitted connection of the auxiliary equipment. A dropping-funnel 6 and valve 7 were used to introduce the liquid reagents into the vessel. The reactor contents could be maintained under an inert atmosphere by means of a stream of nitrogen 8 provided from a cylinder 10 connected to the system through a pressure regulator 12, 14. An Erlenmeyer flask 16 half-full with water provided visual inspection of the outgoing flow. Mixing of the reactor contents was provided by an anchor-type mixer 18 built of 10 mm glass rod and guided by a Teflon bearing. The mixer was driven by a Servodyne Drive unit 20,22 manufactured by Cole-Parmer, Chicago, capable of maintaining of constant speed under variable torque. Jacket temperature control was provided by a Haake, Karlsruhe, Germany, cooling unit 24, Model K11, capable of cooling the circulating fluid down to $-15°$ C. Temperature recovery to the desired level was permitted by a thermostatic bath 26 connected in series with the cooling unit. The connecting hoses were arranged in such a way that the circulating fluid flowed in series through the reactor jacket, the refractometer 28 prisms the cooling unit and the thermostatic bath.

Reactor temperature was measured by a thermocouple immersed in a thermocouple well 30 and connected to a two-pen recorder 32. The recorder also registered the torque required by the mixer. Indices of refraction were measured with an Abbe-3L refractometer 28 manufactured by Zeiss, Germany, that gave direct readings to five significant figures. The temperature control arrangement described before permitted working at prism temperatures up to 70° C. The instrument was carefully calibrated with the test piece supplied by the manufacturer and checked with 1-bromonaphthalene. Viscosity measurements were made with a rotational viscometer manufactured by Contraves, Zurich (Model Rheomat 15), with a range of $1-10^4$ poise. For comparative purposes some measurements were also performed with a Haake Falling Ball viscometer, Model B.

Molecular weight was determined by cryoscopy. The apparatus consisted of a jacketed beaker of 50 ml capacity provided with a variable speed mixer. Cooling was affected by applying vacuum to the jacket and by introducing the beaker into a Thermos bottle containing liquid nitrogen. Temperature readings were taken with a Hewlett-Packard quartz thermometer.

Small-scale runs were done for kinetic purposes using an N.M.R. probe as the reactor and following the reaction by recording its spectrum in a Varian Model XL-100 apparatus.

The experimental setup allowed registering the time change of mixing torque caused by the increase in viscosity. Two runs were performed at 30° C. and 500 rpm to test the influence of the amount of $S_2Cl_2$ added: One with more than the stoichiometric amount for full reaction and the other with less than the stoichiometric amount. Samples were taken during the course of each run and their sulfur content was determined from the measured refractive index. Both runs showed that the sulfur content rose much more rapidly than the viscosity and the mixing torque. With less than the stoichiometric amount of $S_2Cl_2$ the torque and the viscosity rose to an almost constant value towards the end of the reaction (FIG. 3).

The jojoba seeds used were obtained from shrubs grown at the Negev Institute for Arid Zone Research, now a part of the BenGurion University of the Negev. Cold-pressing produced a medium color oil that had the following characteristics: Refractive index (20° C.) 1.4652; iodine value (Wijs), 83.2; melting point, 13.0°; acid number, 6.7; saponification number, 107. The gas chromatographic analysis was performed according to the method suggested by Miwa (1971), namely 3% OV-1 on Gas Chrom Q, 100-200 mesh, stainless steel column of 100 cm long and 0.2 cm i.d., temperature programming of 3°/min between 275° and 300°, injection port 350°, flame ionization oven 380°, Packard-Becker Model 417 chromatograph. The following results were obtained: $C_{34}$ 0.1%; $C_{36}$ 1.6%; $C_{38}$ 7%; $C_{40}$ 32%; $C_{42}$ 49%; $C_{44}$ 9%; $C_{46}$ 0.9%; $C_{48}$ 0.1%. The oil was bleached by adding 2% of active earth, heating to 80° C. for 3 hours and filtering.

About 400 ml of jojoba oil with or without solvent, were introduced into the reactor through port 32 and the mixing system 20 started. The desired agitation speed was attained with the help of control 22 on the Servodyne unit. The contents were heated to the operating temperature by the heating fluid while the temperature was being recorded. When the desired temperature was achieved the system was purged with nitrogen by opening valves 12 and 14 and noting that the gas was slowly bubbling through the water in beaker 16. At this stage the desired amount of $S_2Cl_2$ was introduced into dropping-funnel 6 and its addition started by opening valve 7. This was considered the start of the run. The operating technique for direct addition of $S_2Cl_2$ was similar, except that the reagent was added in one portion through port 32. Several samples were taken during the course of the reaction by introducing a glass rod into the reactor; the attached fluid was examined in the refractometer.

For adiabatic operation the cooling fluid entrance was closed and vacuum applied to the jacket. The desired amount of $S_2Cl_2$ was added in one portion as described. The run was continued until a new, higher level temperature, was attained.

Most of the runs with solvents were performed in the N.M.R. apparatus. Solutions of appropriate concentration were prepared by mixing the desired volumes of solvents and oil with the help of a 2-ml syringe. Adequate amounts of tetramethylsilane (T.M.S.) and solutions were added to the probe and the spectrum of the mixtures recorded. The area of the double bond peak was obtained from the integrator reading. The probe was pulled out and 0.1 ml of $S_2Cl_2$ were added with the aid of a syringe. The probe was rapidly replaced in the apparatus and the time recorded with a stop watch. At predetermined time intervals the height and area of the double bond were recorded. Runs at temperatures different from room temperature were performed in a similar manner, the temperature level was determined by observing the shift of methylene glycol.

The more detailed practice of the present invention is illustrated by the following examples wherein parts are given by weight unless otherwise specified. These examples are illustrative only and are not intended to limit the invention in any way except as indicated by the appended claims.

In the following examples sulfur and chlorine content was determined according to A.S.T.M. method E-443 (1973) with the following minor modifications: Sample size was between 20–50 mg, the combustion flask contained 40 ml of 0.05 N KOH, with some drops of $H_2O_2$. After $SO_2$ absorption the solution was titrated with barium acetate 0.1 N in propanol. The indicator was a 0.1% aqueous solution of 50 ml Carboxyarsenzo, 45 ml Bromophenol Blue and 1 ml Methylene Blue, and the end point was a change in color from light blue to deep blue. Iodine values were determined by A.S.T.M. Method D1959-69 and by N.M.R. spectroscopy.

EXAMPLE 1

To 400 ml jojoba oil are added dropwise 40 ml sulfur monochloride at 40° C., during 15 minutes. The reaction was carried out in a glass reactor equipped with a mixer operating at 500 r.p.m. After addition of the sulfur monochloride the mixture remained for 2 hours at 40° C., under agitation. The sulfurized product contains 8.1% sulfur and 9.32 chlorine, has a molecular weight of 3000-3200 and an I.V. of 8.

EXAMPLE 2

To 400 ml jojoba oil at room temperature are added 35 ml of sulfur monochloride, in one portion, under agitation. After half an hour the sulfurized oil contains 6.65% sulfur and 7.05% chlorine, has a molecular weight of 1700 and an I.V. of 15.

EXAMPLE 3

To 250 ml oil in 300 ml benzene was added 22 ml $S_2Cl_2$ over a period of 5 minutes with stirring. The temperature during the reaction was kept at 30° C. with a cooling bath. After completing the addition of $S_2Cl_2$, the reaction mixture was stirred for 120 minutes. The solvent was evaporated by means of a rotavapor and the remaining product was a viscous reddish liquid having an I.V. of 25.

The sulfur content was 6.2%; the chlorine content was 6.7%, and the molecular weight was 1400.

EXAMPLES 4-7

In a similar manner to that described in examples 1-3 above there were prepared and tested sulfohalogenated jojoba oils having the following sulfur and chlorine content:

|    | % sulfur | % Cl |
|----|----------|------|
| 4. | 3.01     | 3.38 |
| 5. | 6.45     | 6.80 |

-continued

| | % sulfur | % Cl |
|---|---|---|
| 6. | 7.10 | 7.49 |
| 7. | 7.70 | 8.61 |

Viscosity determinations on the above sulfochlorinated jojoba oils gave the following results.

| | Viscosity Centistrokes at 100° F | Viscosity Centistrokes at 210° F |
|---|---|---|
| 4. | 100.76 | 16.78 |
| 5. | 1,888 | 154.39 |
| 6. | 4,462 | 266.3 |
| 7. | 21,680 | 1057 |

The above oils were subjected to the Falex EP test wherein oils from the above examples were diluted to form samples containing 0.1, 0.2, 0.5, 1.0 and 2.5 percent sulfur. The Falex siezure loads attained were as follows:

| Dilution, Wt % S | 4 | 5 | 6 | 7 |
|---|---|---|---|---|
| 0.1 | 500 | 750 | 750 | 4500 |
| 0.2 | 500 | 750 | 4500 | 4500 |
| 0.5 | 750 | 4500 | 4500 | 4500 |
| 1.0 | 4500 | 4500 | 4500 | 4500 |
| 2.5 | 4500 | 4500 | 4500 | 4500 |

As is known the rating of 4500 lbs is the highest attainable with the above test. As can be seen from the above results there seems to be no middle ground in that the sample either fails if present in insufficient quantities (500 and 750 ratings) or passes with the highest rating recordable.

The same samples were subjected to the Four-Ball antiwear test wherein the tester was used under the following conditions:

1 hr/1200 RPM/75° C./40Kg.

The results were as follows in average wear diameter (mm).

| Dilution Wt % S | 4 | 5 | 6 | 7 |
|---|---|---|---|---|
| 0.1 | 0.574 | 0.715 | 0.580 | 0.520 |
| 0.2 | 0.584 | 0.661 | 0.563 | 0.524 |
| 0.5 | 0.787 | 0.613 | 0.535 | 0.506 |
| 0.1 | 0.660 | 0.566 | 0.550 | 0.512 |
| 2.5 | 0.415 | 0.439 | 0.635 | 0.552 |

Blank-Naphthenic oil — 0.838 mm.

As can be seen from comparing the above results with published figures for sulfurized oils the scar attained in the Four-Ball anti-wear test are generally smaller than those attained with sulfurized oils and the Falex seizure loads obtained are much higher, which is unexpectedly superior and excellent lubricating behaviour.

While particular embodiments of the invention have been described it will be evident to those skilled in the art that the present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A non-factice sulfohalogenated jojoba oil characterized by a M.W. under 4,500, and an iodine value greater than 5, a sulfur content below 8.7% by weight and having a sulfur to halogen mole ratio of about 1.1:1.0 to about 1.0:1.1.

2. A sulfohalogenated jojoba oil in accordance with claim 1 wherein the sulfur content is between about 6.5 and 8.5%.

3. A liquid sulfohalogenated jojoba oil in accordance with claim 1 wherein the sulfur content is between about 7 and 8%.

4. A sulfohalogenated jojoba oil in accordance with claim 1 wherein the jojoba oil is sulfochlorinated.

5. A sulfohalogenated jojoba oil in accordance with claim 1 wherein the jojoba oil is sulfobrominated.

6. A lubricating oil comprising a sulfohalogenated jojoba oil in accordance with claim 1 as an additive therein.

7. A process for preparing a non-factice sulfohalogenated jojoba oil in accordance with claim 1 wherein each mole of jojoba oil is reacted with less than one mole of sulfurhalide.

8. A process in accordance with claim 7 wherein sulfur monochloride is used.

9. A process in accordance with claim 7 wherein sulfur monobromide is used.

10. A process in accordance with claim 7 wherein the sulfohalogenation is conducted in the presence of a cyclic solvent.

11. A process in accordance with claim 10 wherein the cyclic solvent has a dielectric constant between 2 to 15.

12. A process in accordance with claim 10 wherein the solvent is selected from the group consisting of benzene, chlorobenzene, 1,4-dioxane and dichlorobenzene.

* * * * *